United States Patent [19]

Knowles et al.

[11] Patent Number: 5,464,567
[45] Date of Patent: Nov. 7, 1995

[54] PHOTOCHROMIC TETRAPHENYL NAPHTHODIPYRANS

[75] Inventors: David B. Knowles, Apollo; Barry V. Gemert, Murrysville, both of Pa.

[73] Assignee: Transitions Optical, Inc., Pinellas Park, Fla.

[21] Appl. No.: 225,033

[22] Filed: Apr. 8, 1994

[51] Int. Cl.$^6$ .......................... G02B 5/23; C07D 311/78
[52] U.S. Cl. ............................... 252/586; 549/384
[58] Field of Search ............................ 252/586; 549/384

[56] References Cited

U.S. PATENT DOCUMENTS

| | | | |
|---|---|---|---|
| 3,567,605 | 3/1971 | Becker | 204/158 |
| 4,563,458 | 1/1986 | Widdig et al. | 514/253 |
| 4,818,096 | 4/1989 | Heller et al. | 351/163 |
| 4,826,977 | 5/1989 | Heller et al. | 544/70 |

FOREIGN PATENT DOCUMENTS

| | | |
|---|---|---|
| 246114 | 11/1987 | European Pat. Off. . |
| 250193 | 12/1987 | European Pat. Off. . |
| 294056 | 12/1988 | European Pat. Off. . |

OTHER PUBLICATIONS

Padwa et al., J. Org. Chem., vol. 40, No. 8, 1975, p. 1142.

*Primary Examiner*—Nicky Chan
*Attorney, Agent, or Firm*—Irwin M. Stein

[57] ABSTRACT

Described are novel reversible photochromic naphthopyran compounds which have two phenyl moieties adjacent to each oxygen of each pyran ring. The substituents on each pair of phenyl moieties mirror one another when the phenyl groups are substituted. The naphthodipyrans are prepared from β,β-dihydroxynaphthalene compounds.

12 Claims, No Drawings

PHOTOCHROMIC TETRAPHENYL NAPHTHODIPYRANS

FIELD OF THE INVENTION

The invention relates to photochromic compounds for use in plastic ophthalmic lenses or other related articles.

BACKGROUND OF THE INVENTION

Photochromic plastic materials, particularly plastic materials for optical applications, have in recent years attracted growing commercial interest due to their light weight in comparison to glass. When exposed to light radiation containing ultraviolet (UV) rays, such as the ultraviolet radiation in sunlight or the light of a mercury lamp, photochromic compounds exhibit a reversible change in color. When the ultraviolet radiation is discontinued, the photochromic compounds return to their original color or colorless state. Ideal photochromic compounds for use in optical applications change color efficiently upon exposure to near ultraviolet light, resist bleaching in white light and have a relatively fast ability to fade at ambient temperature.

A variety of photochromic compounds have been proposed for use in applications in which a sunlight-induced reversible color change or darkening is desired. U.S. Pat. No. 3,567,605 to Becker describes a series of pyran derivatives, including certain benzopyrans and naphthopyrans. U.S. Pat. No. 4,563,458 describes chroman and chromene compounds intended for use in pharmaceutical compositions. European Patent Publication 246,114 and U.S. Pat. No. 4,826,977 describe a series of photochromic spiropyrans in which an adamantane group is attached at the position adjacent to the oxygen in the pyran ring. U.S. Pat. No. 4,818,096 and European Patent Publication 250,193 describe photoreactive plastic lenses that include the photochromic spiropyrans of European Patent Publication 246,114 in combination with a blue photochromic benzopyran or naphthopyran having an aminophenyl substituent at the position adjacent to the oxygen in the pyran ring. The '096 patent also discloses 2,2,8,8-tetraaryl-2H,8H-[1,2-b:5,6-b'] dipyran, a compound based upon 1,5-dihydroxynaphthalene. European Patent Publication 294,056 describes a process for producing a polyurethane plastic having photochromic properties; the photochromic compounds contained in the plastic include, among others, a naphthopyran derivative in which the pyran ring is substituted at the position adjacent to the oxygen in the pyran ring with di(p-methoxyphenyl) substituents.

Padwa et al. in *J. Org. Chem.*, Volume 40, No. 8, 1975, page 1142, describes the investigation of photochemical reactions of 2,2-dimethylbenzopyran and related compounds, and identifies fatigue products and suggests pathways to the ring-opened colored intermediates and the phenolic degradation product. The authors do not suggest ways in which the compounds might be improved, nor any modification that might be made to the structure of the known pyran compounds.

Inadequate fade rate has plagued—to a greater or lesser degree—certain of the prior art photochromic compounds. A need therefore remains for photochromic compounds which exhibit adequate fade characteristics yet preserve the other desired characteristics for a photochromic compound.

SUMMARY OF THE INVENTION

In order to meet this need, certain naphthodipyran compounds have been identified which demonstrate desirable photochromic characteristics including adequate fade rates. These naphthodipyrans, or naphtho-bis-pyrans, may be represented by graphic formula I:

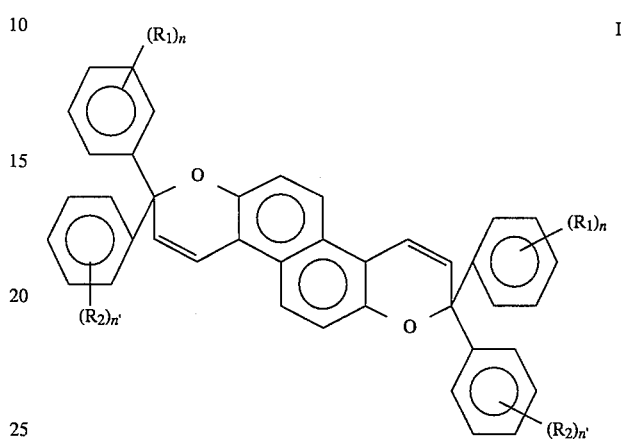

The naphthodipyrans of graphic formula I have two phenyl moieties adjacent to the oxygen of each pyran ring. Furthermore, for those compounds in which the phenyl groups attached to each pyran ring are further substituted, the substituents on each pair of phenyl groups mirror one another. The phenyl substituents $R_1$ and $R_2$ may each be $(C_1-C_5)$ alkyl, $(C_1-C_5)$ alkoxy, halogen (usually F or Cl), hydroxy, aryl, e.g., phenyl, methacrylyl, acryloxy $(C_1-C_4)$ alkyl, methacryloxy $(C_1-C_4)$ alkyl, or a primary, secondary or tertiary amino group. The letters n and n' each may be an integer of from 0 to 2.

DETAILED DESCRIPTION OF THE INVENTION

In recent times, photochromic plastic materials, particularly plastic materials for optical applications, have attracted growing commercial interest due to their light weight in comparison to glass. Ideal photochromic compounds for use in optical applications—such as traditional plastic eyeglass lenses—color efficiently upon exposure to near ultraviolet light, resist bleaching in white light and have an acceptably fast fade rate.

In accordance with the present invention, there have been developed certain novel reversible photochromic naphthopyran compounds which have acceptable fade characteristics and other desirable photochromic properties. These naphthodipyrans, or naphtho-bis-pyrans, are tetraphenyl substituted or, in other words, have two phenyl moieties adjacent to the oxygen of each pyran ring. Furthermore, each pyran ring is identically substituted.

Although the formula for the present tetraphenyl naphthodipyrans may be generally represented by graphic formula I:

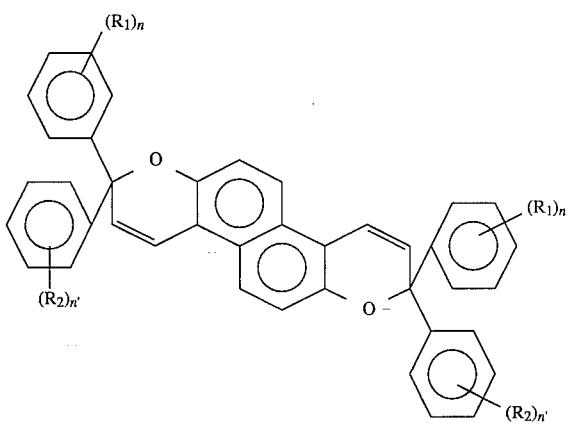

3,3,9,9-tetraphenyl-3H,9H-naphtho[2,1-b:6,5-b']-dipyran two variations on the general formula (formulas II and III) are also within the scope of the present invention:

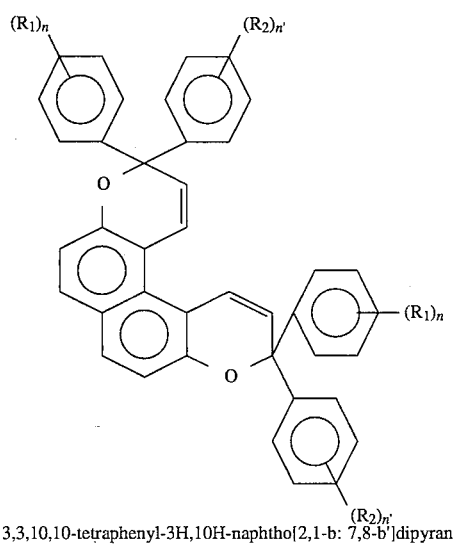

3,3,10,10-tetraphenyl-3H,10H-naphtho[2,1-b: 7,8-b']dipyran

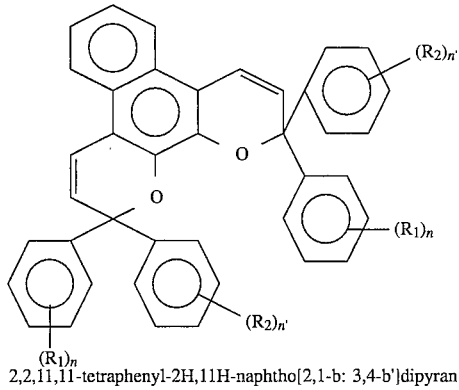

2,2,11,11-tetraphenyl-2H,11H-naphtho[2,1-b: 3,4-b']dipyran

The three tetraphenyl naphthodipyrans are the same except that a different isomer of β,β-dihydroxynaphthalene is used as the starting material, namely, 2,6-dihydroxynaphthalene, 2,7-dihydroxynaphthalene and 2,3-dihydroxynaphthalene, respectively, as is discussed further below.

The substituents $R_1$ and $R_2$ may each be ($C_1$–$C_5$) alkyl, ($C_1$–$C_5$) alkoxy, halogen (usually F or Cl), hydroxy, aryl, e.g., phenyl, methacrylyl, acryloxy ($C_1$–$C_4$) alkyl, methacryloxy ($C_1$–$C_4$) alkyl or a primary, secondary or tertiary amino group. The letters n and n' each may be the integers 0, 1 or 2 and n +n' may equal 0–4, but preferably equals 0–2. Generally, it is preferred that the substituents be in the meta or para positions; ortho substitution is not preferred.

In order to obtain the desired results of the present invention; namely, a desirable fade rate, it is important to select the correct dihydroxynaphthalene starting material. For example, the unsubstituted 2,2,8,8-tetraphenyl-2H, 8H-[1,2-b:5,6-b']dipyran, which is prepared from 1,5-dihydroxynaphthalene and is disclosed in U.S. Pat. No. 4,818,096, gives a very long and unacceptable fade rate, which the present invention sought to and has overcome.

The tetraphenyl naphthodipyrans of the present invention are those based on β,β-dihydroxynaphthalene compounds, specifically, 2,3-dihydroxynaphthalene, 2,6-dihydroxynaphthalene or 2,7-dihydroxynaphthalene. In other words, the present compositions are not prepared from α,α-dihydroxynaphthalenes or from α,β-dihydroxynaphthalenes. This use of the β,β-dihydroxynaphthalene starting materials exclusively contributes to the improved fade rates of the compounds of the present invention.

Generally, the synthesis of the present tetraphenyl naphthodipyrans includes the steps of reacting the appropriately substituted or unsubstituted 1,1-diphenyl- 2-propyn-1-ol in an organic solvent, Usually toluene, with one of the following dihydroxynaphthalenes: 2,3-dihydroxynaphthalene, 2,6-dihydroxynaphthalene or 2,7-dihydroxynaphthalene, in a mole ratio of 2:1, respectively. The reaction is conducted in the presence of a catalytic amount of a suitable acid catalyst such as para-toluenesulfonic acid and the reaction proceeds under heat over a period of a few to several hours. The reaction once completed may be worked-up by means known in the art, such as by quenching in aqueous sodium hydroxide. The reaction product is isolated by separating the organic fraction, drying it by conventional means, such as with magnesium sulfate and removing the solvent under vacuum, such as by use of a rotary evaporator. Generally, the product which is isolated in its crystalline state, can be purified by washing with a solvent, such as diethyl ether.

The tetraphenyl naphthodipyrans of the present invention change color generally to yellow-to-red, on exposure to ultraviolet radiation, with the more extensively substituted compositions exhibiting the bathochromic shift to red.

The present tetraphenyl naphthodipyrans are suitable for use in appropriate applications in which organic photochromic substances may be employed, such as optical lenses, e.g., ophthalmic and plano lenses, face shields, goggles, ski goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired.

Commercially available photoreactive inorganic glass lenses containing silver halide particles darken to a gray or brown color in sunlight. In order to achieve a similar gray or brown color on exposure to ultraviolet (UV) light, it is contemplated that the present tetraphenyl naphthodipyrans be used in combination with other appropriate complementary organic photochromic materials. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than for photochromic lenses. Further, although gray and brown shades are the desired shades for ophthalmic lenses, the compounds of the present invention may be combined with any suitable complementary photochromic compound to produce any desired shade other than gray or brown.

Particularly contemplated classes of complementary organic photochromic compounds that may be used in combination with the naphthopyrans of the present invention include: purple/blue spiro(indolino) benzoxazines, such as those described in U.S. Pat. No. 4,816,584; spiro(indolino) pyridobenzoxazine photochromic compounds, such as those described in U.S. Pat. No. 4,637,698; and spiro(indolino) naphthoxazines, such as those described in U.S. Pat. Nos. 3,562,172, 3,578,602, 4,215,010 and 4,342,668. All of the aforedescribed organic photochromic compounds are reported to exhibit a color change of from colorless to purple/blue on exposure to ultraviolet light. The disclosures of said U.S. patents are hereby incorporated herein by reference.

Other contemplated complementary organic photochromic compounds that are reported to exhibit a color change of from colorless to yellow/orange when exposed to UV light may be used in combination with the naphthopyran compounds of the present invention to augment the yellow/orange color of those activated photochromic compounds. Such complementary yellow/orange compounds include: benzopyrans and naphthopyrans having a spiro adamantylene group in the 2-position of the pyran ring, such as those described in U.S. Pat. No. 4,826,977, and naphthopyran compounds such as those described in U.S. Pat. No. 5,066,818. The disclosures of such U.S. patents are also hereby incorporated herein by reference.

The naphthopyran compounds of the present invention may be used in admixture with or in conjunction with the aforedescribed complementary or augmenting organic photochromic compounds in amounts and in a ratio such that an organic host material to which the mixture of photochromic compound(s) is applied or in which they are incorporated exhibit a substantially neutral color when activated with unfiltered sunlight, i.e., as near a neutral gray or brown color as is possible given the colors of the activated photochromic compounds. The relative amounts of the photochromic compounds used will vary and depend in part upon the relative intensities of the color of the activated species of such compounds.

For example, the naphthopyran compounds of the present invention may be combined with one or more of the aforedescribed purple/blue spirooxazine- and/or pyran-type organic photochromic compounds in amounts and in ratios such that an organic host material to which the mixture of compounds is applied or in which they are then incorporated exhibits a near-brown color. Generally, the weight ratio of each of the aforedescribed spirooxazine- and pyran-type compound(s) to the naphthopyran compound(s) of the present invention will vary from about 1:3 to about 3:1, e.g., between about 1:2 or 0.75:1 and about 2:1.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/X+Y+Z$ and $y=Y/X+Y+Z$. Color as described in the CIE system can be plotted on a chromaticity diagram, usually a plot of the chromaticity coordinates x and y. See pages 47–52 of *Principles of Color Technology*, by F. W. Billmeyer, Jr. and Max Saltzman, Second Edition, John Wiley and Sons, N.Y. (1981).

The amount of photochromic substance or composition containing it applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substance. Typically, the more compound applied or incorporated, the greater is the color intensity.

Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Expressed differently, the total amount of photochromic substance incorporated into or applied to an optical host material may range from about 0.15 to about 0.35 milligrams per square centimeter of surface to which the photochromic substance(s) is incorporated or applied.

Photochromic compounds of the present invention, mixtures of such compounds with other photochromic compounds, or compositions containing the same may be applied to or incorporated into a host material by various methods described in the art. Such methods include: dissolving or dispersing the photochromic substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to embrace, nonexclusively, permeation of the photochromic substance alone into the host material, solvent assisted transfer absorption of the photochromic substance into a porous polymer, vapor phase transfer, and other such transfer mechanisms. See U.S. Pat. No. 5,066,818, Column 14, line 41 to Column 15, line 25 for examples of the above methods.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e, the open form. Further, the resin color should not be such that it masks the color of the activated form of the photochromic substance, i.e., so the change in color is readily apparent to the observer. Preferably, the host material article is a solid transparent or optically clear material.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or to absorb a particular wavelength of incident light. In another embodiment, the dye may be selected to provide a desired hue to the host matrix when the photochromic substance is in an unactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superimposed as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

Singlet oxygen quenchers that may be used as stabilizers include complexes of nickel (2+), i.e., $Ni^{2+}$, with an organic ligand, cobalt (III) tris-di-n-butyldithiocarbamate, cobalt (II) diisopropyldithiocarbamate and nickel diisopropyldithiophosphate. Such singlet oxygen quenchers are used in stabilizing amounts.

Preferred are complexes of $Ni^{2+}$ such as [2,2-thiobis[4-(1, 1,3,3-tetramethylbutyl) phenolato] (butylamine)] nickel, which is sold under the tradename of CYASORB UV 1084; nickel [O-ethyl (3,5-di-tert-butyl-4-hydroxybenzyl)] phosphonate, which is sold under the tradename IRGASTAB 2002; nickel dibutyldithiocarbamate, which is sold under the tradename RYLEX NBC; bis[2,2'-thiobis-4-(1,1,3,3-tetramethylbutyl)phenolato]nickel, which is sold under the tradename UV-CHEK AM 101; nickel diisopropyldithiophosphate and other $Ni^{2+}$ complexes sold under the tradenames of UV-CHEK AM 105, UV-CHEK 126 and UV-CHEK AM 205.

Hindered amine light stabilizers that may be used include bis(2,2,6,6-tetramethyl-4-piperidinyl) sebacate, which is sold under the tradename TINUVIN 770; bis( 1,2,2,6,6-pentamethyl-4-piperidinyl) sebacate, which is sold under the tradename TINUVIN 765; di(1,2,2,6,6-pentamethyl- 4-piperidinyl)butyl-(3', 5'-ditertiary-butyl-4-hydroxybenzyl)malonate, which is sold under the tradename TINUVIN 144; poly[(6-[(1,1,3,3-tetramethylbutyl) amino]- 1,3,5-triazine-2, 4-diyl)-(6-[2,2,6,6-tetramethyl- 4-piperidinyl]-amino-hexamethylene)], which is sold under the tradename CHIMASSORB 944; and poly[[6-(morpholino)-s-triazine- 2,4-diyl] [16-(2,2,6,6-tetramethyl-4-piperdyl)amino]hexamethylene], which is sold under the tradename CYASORB 3346. Other hindered amine light stabilizers that may be used are those sold under the tradename TINUVIN 622, SPINUVEX A-36 and HOSTAVIN TMN 20. Such stabilizers are used in stabilizing amounts.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent by weight of the foregoing stabilizers may be used (alone or in combination) to improve the light fatigue resistance of the photochromic materials.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material, e.g., materials suitable for optical applications, such as plano and ophthalmic lenses, windows, automotive transparencies, e.g., windshields, aircraft transparencies, plastic sheeting, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkyl acrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate) and acrylate monomers.

Transparent copolymers and blends of transparent polymers are also suitable as host materials. Preferably, the host material is an optically clear polymerized organic material prepared from a polycarbonate resin, such as the carbonate-linked thermoplastic resin derived from a bisphenol, such as bisphenol A, and phosgene, which is sold under the trademark LEXAN, i.e., poly(4-phenoxy-4'-phenoxy-carbonyl-2, 2-propane); a poly(methyl methacrylate), such as the material sold under the trademark PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. No. 4,360,653; cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., methods described in U.S. Pat. Nos. 2,370,567 and 2,403,113.

The unsubstituted compounds shown in graphic formulae I–III (i.e., n+n'=0) were prepared according to Examples 1–3, below. To prepare substituted tetraphenyl naphthodipyrans shown in graphic formulae I, II or III, (i.e., n+n'≠0) the 1,1-diphenyl-2-propyn-1-ol need only contain the appropriate substituents. Substituted propynols can be prepared by reacting sodium acetylide with the appropriate benzophenone dissolve in a solvent such as tetrahydrofuran. Many benzophenones are commercially available. Furthermore, the preparations disclosed in Examples 1–3 are illustrative only and alternative methods for synthesizing them will be readily apparent to those of ordinary skill in the art. The essence of the present invention does not reside in the synthesis of the disclosed compounds, but instead in the identification of improved fade rate of the disclosed photochromic compounds without loss of other desired characteristics.

Although not intended to be limiting, the following examples are helpful in describing various aspects of the present invention.

EXAMPLE 1

The unsubstituted compound, i.e., n and n' are 0, shown in graphic formula I was prepared as follows: Five (5.0) grams (0.031 mole) of 2,6-dihydroxynaphthalene were added to 300 milliliters of toluene containing 13.0 grams of 1,1-diphenyl-2-propyn-1-ol (0.062 mole). A catalytic amount of para-toluenesulfonic acid was added to the stirred solution and the mixture heated to between 30° C. and 35° C. for 4 hours. The reaction was quenched in 20 weight percent of aqueous sodium hydroxide. The organic layer of toluene containing the product was separated, dried over magnesium sulfate and the solvent removed under vacuum. The resulting crystals were washed with diethyl ether and suction filtered to yield 2.0 grams of 3,3,9,9-tetraphenyl-3H,9H-naphtho[2,1-b:6,5b']dipyran (melting point= 202°–205° C.), whose structure was consistent with a nuclear magnetic resonance (NMR) spectrum of the product.

EXAMPLE 2

The unsubstituted compound shown in graphic formula II, i.e., n and n' are 0, was prepared as follows: Five (5.0) grams (0.031 mole) of 2,7-dihydroxynaphthalene were added to 300 milliliters of toluene containing 13.0 grams of 1,1-diphenyl-2-propyn-1-ol (0.062 mole). A catalytic amount of para-toluenesulfonic acid was added to the stirred solution and the mixture heated to between 30° C. and 35° C. for 4 hours. The reaction was quenched in 20 weight percent of aqueous sodium hydroxide. The organic layer of toluene containing the product was separated, dried over magnesium sulfate and the solvent removed under vacuum. The resulting crystals were washed with diethyl ether and suction filtered to yield 2.0 grams of 3,3,10,10-tetraphenyl-3H,10H-naphtho[2,1-b:7,8b']dipyran (melting point=225°–228° C.), whose structure was consistent with a nuclear magnetic resonance spectrum of the product.

EXAMPLE 3

The unsubstituted compound shown in graphic formula III, i.e., n and n' are 0, was prepared as follows: Five (5.0) grams (0.031 mole) of 2,3-dihydroxynaphthalene were added to 300 milliliters of toluene containing 13.0 grams of 1,1-diphenyl-2-propyn-1-ol (0.062 mole). A catalytic amount of para-toluenesulfonic acid was added to the stirred solution and the mixture heated to between 30° C. and 35° C. for 4 hours. The reaction was quenched in 20 weight percent of aqueous sodium hydroxide. The organic layer of toluene containing the product was separated, dried over magnesium sulfate and the solvent removed under vacuum. The resulting crystals were washed with diethyl ether and suction filtered to yield 2.0 grams of 2,2,11,11-tetraphenyl-2H,11H-naphtho[2,1-b:3,4b']dipyran (melting point= 233°–235° C.), whose structure was consistent with a nuclear magnetic resonance spectrum of the product.

EXAMPLE 4

Photochromicity testing of the compositions prepared in Examples 1–3 was conducted by dissolving 25 milligram samples of each individually, in 2.0 grams of a solution containing 10 weight percent ethyl cellulose in toluene. The naphthodipyran compound was dissolved by warming and stirring the solution on a steam bath. Approximately 2.0 grams of the resultant solution was deposited on the edge of a 75 by 25 millimeter (mm) glass slide. Using an 8 mil draw down bar, a layer of photochromic resin solution was placed evenly on the slide and permitted to dry.

The slides prepared as described above were tested for photochromic response rates on an optical bench. The samples were illuminated by a 150 watt Xenon lamp fitted with a copper sulfate bath and a neutral density filter at an intensity of about one sun. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The following test values were obtained and are tabulated in Table 1. The delta OD/Min, which represents the sensitivity of the photochromic compound's response to ultraviolet light, was measured using photopic filters on the silicon detector. The response of the filtered detector approximated the luminosity curve. The delta OD/Min was measured over the first five (5) seconds of UV exposure, then expressed on a per minute basis. The delta OD @ Saturation was taken under identical conditions as the delta OD/Min, except UV exposure was continued until no further delta OD could be detected. Lambda max is the wavelength in the visible spectrum at which the maximum absorption of the activated (colored) form of the photochromic compound in ethyl cellulose occurs. The Bleach Rate T ½ is the time interval in seconds for the absorbance of the activated form of the naphthopyran in the test polymers to reach one half the highest absorbance at room temperature (72° F., 22.2° C.) after removal of the source of activating light.

| COMPOUND EXAMPLE | LAMBDA MAX | DELTA OD/MIN (SENSITIVITY) | DELTA OD @ SATURATION | BLEACH RATE T ½ (Sec.) |
|---|---|---|---|---|
| 1 | 481 nm | 0.48 | 0.27 | 283 |
| 2 | 411 nm | 0.34 | 0.20 | 155 |
| 3 | 411 nm | 0.27 | 0.20 | 608 |

Comparative Example 1

By contrast to the above tested characteristics of the present photochromic substances, prior art photochromic compositions such as those disclosed in U.S. Pat. No. 4,818,096 to Heller et al. do not demonstrate comparably short Bleach T ½ (Sec.) values. This was documented as follows.

1–5-dihydroxynaphthalene (4.0 grams, 0.025 mole) was added to 300 milliliters of toluene containing 2.2 equivalents of 1,1-diphenyl-2-propyn-1-ol (11.4 grams, 0.55 mole). A catalytic amount of dodecylbenzenesulfonic acid was added to the stirred solution and the mixture heated to 50° C. for three hours. The reaction mixture was washed once with distilled water and then extracted with 20 weight percent aqueous sodium hydroxide. The organic layer of toluene containing the product was separated, and the solvent removed under vacuum and the residue was purified on a silica gel column. The photochromic fractions were collected and the solvent removed under vacuum to yield 0.5 gram of 2,2,8,8-tetraphenyl-2H,8H[1,2-b:5,6-b']dipyran (melting point greater than 250° C.) whose structure was consistent with a nuclear magnetic resonance spectrum of the product.

The following test values were obtained and are tabulated in Table 2. The test values were obtained in the same manner described for Example 4.

| COMPOUND EXAMPLE | LAMBDA MAX | DELTA OD/MIN (SENSITIVITY) | DELTA OD @ SATURATION | BLEACH RATE T ½ (Sec.) |
|---|---|---|---|---|
| Comp've 1 | 508 nm | 0.79 | 0.95 | >1800 |

In view of the results summarized in Table 2, the fade rate for the naphthodipyran of Comparative Example 1 is much slower (>1800 Sec.) than any of the comparable fade rates of the compounds of the present invention, as shown in Table 1; namely, 283, 155 and 608 seconds, respectively. The difference is believed to be attributable to the present compounds' being based upon β,β-dihydroxynaphthalene exclusively, and not α,β-dihydroxynaphthalene or α,α-dihydroxynaphthalene.

Although the present invention has been described with reference to the specific details of particular embodiments thereof, it is not intended that such details be regarded upon the scope of the invention except insofar as and to the extent that they are included in the accompanying claims.

We claim:

1. A naphthodipyran selected from the group consisting of 3,3,9,9-tetraphenyl-3H,9H-naphtho[2,1-b: 6,5-b']dipyran, 3,3,10,10-tetraphenyl-3H,10H-naphtho[2,1-b: 7,8-b']dipyran and 2,2,11,11-tetraphenyl-2H,11H-naphtho[2,1-b: 3,4-b']dipyran.

2. A tetraphenyl naphthodipyran selected from the group consisting of naphthopyrans represented by the following graphic formulae:

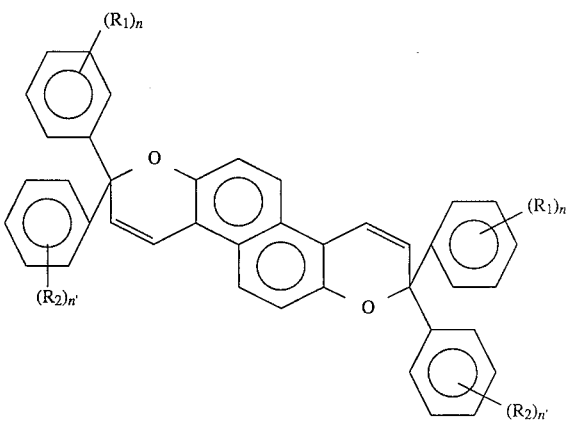

-continued

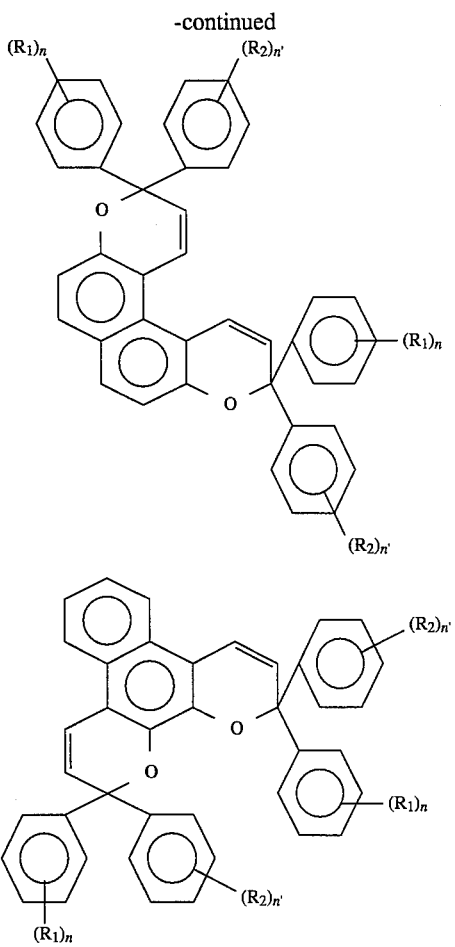

wherein $R_1$ and $R_2$ are each selected from the group consisting of $(C_1-C_5)$ alkyl, $(C_1-C_5)$ alkoxy, halogen, hydroxy, phenyl, methacrylyl, acryloxy $(C_1-C_4)$ alkyl and methacryloxy $(C_1-C_4)$ alkyl, and n and n' are each an integer of from 0 to 2.

3. The naphthodipyran according to claim 2 wherein $R_1$ and $R_2$ are the same and the sum of n and n' is an integer of from 0–2.

4. The naphthodipyran according to claim 3 wherein the substituents $R_1$ and $R_2$ are each in the meta or para position.

5. The naphthodipyran of claim 2 wherein the sum of n and n' is an integer of from 0 to 2.

6. The naphthodipyran of claim 2 wherein $R_1$ and $R_2$ are each selected from $(C_1-C_5)$alkyl, $(C_1-C_5)$alkoxy and halogen and the sum of n and n' is an integer of from 0 to 2.

7. The naphthodipyran of claim 3 wherein $R_1$ and $R_2$ are selected from $(C_1-C_5)$alkyl, $(C_1-C_5)$alkoxy, chloro and fluoro 8. A photochromic article comprising an organic host material and a photochromic amount of a naphthodipyran compound of claim 2.

9. The photochromic article according to claim 8 wherein said organic host material is selected from the group consisting of polyol(allyl carbonate) homopolymers, polyol(allyl carbonate) copolymers, polyfunctional acrylate homopolymers, polyfunctional acrylate copolymers, polyacrylates, poly(alkyl acrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, poly(ethylene terephthalate), polystyrene, copoly(styrene-methyl methacrylate), copoly(styrene-acrylonitrile), polyvinylbutyral, diallylidene pentaerythritol homopolymers and diallylidene pentaerythritol copolymers.

10. A photochromic article according to claim 8 wherein the polymerized organic host material further comprises a photochromic amount of a photochromic substance selected from the group consisting of spiro(indolino) naphthoxazines, spiro(indolino) pyrido benzoxazines and spiro(indolino) benzoxazines.

11. The photochromic article according to claim 10 wherein said article is a lens.

12. The photochromic article of claim 9 wherein the naphthodipyran is selected from the naphthodipyrans of claim 1.

* * * * *